US009913478B2

(12) United States Patent
Morales-Morales et al.

(10) Patent No.: US 9,913,478 B2
(45) Date of Patent: Mar. 13, 2018

(54) ORGANIC AND ENVIRONMENTALLY "GREEN" BIOCIDE COMPOSITIONS AND APPLICATIONS

(71) Applicant: Arrowhead Center, Inc., Las Cruces, NM (US)

(72) Inventors: Hugo A. Morales-Morales, Cd. Meoqui (MX); Geoffrey Battle Smith, Las Cruces, NM (US); Soum Sanogo, Las Cruces, NM (US); Alba Chavez-Dozal, Albuquerque, NM (US)

(73) Assignee: Arrowhead Center, Inc., Las Cruces, NM (US)

( * ) Notice: Subject to any disclaimer, the term of this patent is extended or adjusted under 35 U.S.C. 154(b) by 157 days.

(21) Appl. No.: 14/558,601

(22) Filed: Dec. 2, 2014

(65) Prior Publication Data

US 2016/0073643 A1 Mar. 17, 2016

Related U.S. Application Data

(60) Provisional application No. 61/910,720, filed on Dec. 2, 2013.

(51) Int. Cl.
*A61K 36/53* (2006.01)
*A61K 36/85* (2006.01)
*A61K 36/18* (2006.01)
*A01N 65/22* (2009.01)

(52) U.S. Cl.
CPC .................................... *A01N 65/22* (2013.01)

(58) Field of Classification Search
None
See application file for complete search history.

(56) References Cited

U.S. PATENT DOCUMENTS

| | | | | |
|---|---|---|---|---|
| 1,707,466 | A | 4/1929 | Volck | |
| 5,658,954 | A | 8/1997 | Targosz | |
| 5,955,086 | A * | 9/1999 | DeLuca | A61K 9/2009 424/464 |
| 6,808,717 | B1 | 10/2004 | Bale | |
| 8,188,004 | B2 | 5/2012 | Hsu et al. | |
| 2002/0018820 | A1 | 2/2002 | Pullen | |
| 2005/0196359 | A1 * | 9/2005 | D'Amelio, Sr. | A61K 8/347 424/58 |
| 2005/0214337 | A1 | 9/2005 | McGee et al. | |
| 2006/0165746 | A1 | 7/2006 | Markus et al. | |
| 2007/0014819 | A1 * | 1/2007 | Wu | A61K 9/107 424/400 |
| 2012/0087964 | A1 | 4/2012 | Man et al. | |
| 2013/0078296 | A1 | 3/2013 | Grlica et al. | |

FOREIGN PATENT DOCUMENTS

WO 2011142918 A1 11/2011

OTHER PUBLICATIONS

Website document entitled "Sophisticated Solutions for Simplified Labels" (available at http://www.globalfoodforums.com/wp-content/uploads/2013/11/2013cleanlabel-Ingredion-Diaz.pdf). Dated Oct. 29-30, 2013.*
Cheeke et al. (2006) Journal of Inflammation, 3:6(pp. 1-7).*
Dudai et al. (2008) Proc. II IS on Natural Preserv. in Food, Feed and Cosmetics, Acta Hort. 778 pp. 15-28.*
Kordali et al. (2008) Bioresource Technology 99: 8788-8795.*
B.C. Ministry of Agriculture, The Plant Health Strategy, Jun. 2013.
Chavez, Identification of Xanthomonas Campestris in Japaleno and Its Control Using Mexican Oregano (*Lippia berlandieri*) Essential Oil, Aug. 2008.
Cueto-Wong, et al., "Antifungal Properties of Essential Oil of Mexican Oregano", http://www/scielo.org.mx/scielo.php?pid=S0187-318020100005&script=sci_arttext, Mar. 13, 2010.
Experience-Essential-Oils.com, http://www.experience-essential-oils.com/homemade-insecticides.html, 2010.
Hausbeck, "Phytophthora capsici on Vegetable Crops: Research Progress and Management Challenges", Plant Disease, 2004, 1292-1303.
JH Biotech Company, http://jhbiotech.com/plant-products/, 2013.
Rodriguez-Roj, et al., "Characterization of rosemary essential oil for biodegradable emulsions", Industrial Crops and Products, 2012, 137-140.
Sanogo, et al., "Integrated management of Phytophthora capsici on solanaceous and cucurbitaceous crops: current status, gaps in knowledge and research needs", Can. J. Plant Pathol., 2012, 479-492.
Uchida, "Rhizoctonia solani", http://www.extento.hawaii.edu/kbase/crop/Type/r_solani.htm, 2011.
Yang, et al., "Inhibitory Effects of Essential Oils for Controlling Phytophthora capsici", Plant Disease, 2012, 797-803.
Yang, et al., "Plant-Plant-Microbe Mechanisms Involved in Soil-Borne Disease Suppression on a Maize and Pepper Intercropping System", PLOS One, vol. 9, No. 12: e115052. doi: 10.1371/journal.pone.0115052, Dec. 31, 2014.
Herman, et al., "Essential Oils and Herbal Extracts as Antimicrobial Agents in Cosmetic Emulsion", Indian J Microbiol, vol. 53, No. 2, Springer, Apr. 6, 2013, 232-237.
Manou, et al., "Evaluation of the preservative properties of Thymus vulgaris essential oil in topically applied formulations under a challenge test", Journal of Applied Microbiology, The Society for Applied Microbiology, 1998, 368-376.
Patrone, et al., "In Vitro Synergistic Activities of Essential Oils and Surfactants in Combination with Cosmetic Preservatives Against Pseudomonas airuginosa and *Staphylococcus aureus*", Curr Microbial, Springer, 2010, 237-241.
Wilder, "Oil of Oregano", http://www.natures-pantryny.com/news/store_news.asp?task=store_news+9&storeID=56000b8bc6ea445a8fa064273f3d949, Mar. 2014.

* cited by examiner

*Primary Examiner* — Chris R Tate
*Assistant Examiner* — Russell Fiebig
(74) *Attorney, Agent, or Firm* — Isaac Estrada; Deborah A. Peacock; Peacock Law P.C.

(57) ABSTRACT

Natural, organic, environmentally "green" biocide compositions comprising oregano oil in various natural delivery media.

7 Claims, 8 Drawing Sheets

B.

ORGANIC AND ENVIRONMENTALLY "GREEN" BIOCIDE COMPOSITIONS AND APPLICATIONS

CROSS-REFERENCE TO RELATED APPLICATIONS

This application claims priority to and the benefit of the filing of U.S. Provisional Patent Application Ser. No. 61/910,720, entitled "ORGANIC AND ENVIRONMENTALLY "GREEN" PESTICIDE COMPOSITIONS", filed on Dec. 2, 2013, and the specification thereof is incorporated herein by reference.

BACKGROUND OF THE INVENTION

Field of the Invention (Technical Field)

The present invention relates to organic compositions and more particularly to compositions comprising essential oils and organic surfactants or solidifying agents.

Description of Related Art

Synthetic biocides, while effective, cannot be used in organic farming applications. Additionally, the cost of manufacturing their ingredients translates to their prices, which can be prohibitive for some farmers, particularly in developing nations. For instance, the fungi *Rhizoctonia solani* and *Phytophthora capsici* infect a wide variety of crops around the world. Alfalfa, peanut, soy, lima bean, cucumber, chili peppers, and corn are just a few of the over five hosts of *R. solani* in the United States alone, with many more affected worldwide. *R. solani* can cause collar and root rot, web blights on leaves and pods, callus formation, thickening of the collar area, plant stunting and poor vigor. The Ministry of Agriculture reported in 2011 that more than fifty plant species are susceptible to the adverse effects of *P. capsici*, which include necrotic lesions on vines, fruit rot, leaf wilting and moldy growth. Both *R. solani* and *P. capsici* are aggressive, hardy pathogens. Every year these pathogens devastate the production of crops for many farmers causing millions of dollars in losses. Similarly, plant pathogens such as the bacterium *Xanthomonas campestris* and the nematode *Caenorhabditis elegans* cause severe damage to both agricultural crops and turf grasses and there is a need for environmentally green, natural alternatives to current practices to control these pests.

Similarly, there is need for natural organic biocides for use in animal husbandry and human health applications. There has been a long felt need for biocides comprising natural constituents that are not toxic to humans and animals, and which have comparable effectiveness to that of synthetic biocides. For example, mastitis, caused by various bacteria infecting the teat canals of lactating cows and goats, remains without effective treatment. Also, human skin infections like onychomycosis, the fungal infection of human toenails, is not very effectively treated by synthetic chemicals and there is need for alternate effective, organic treatment ointments.

Embodiments of the present invention solve these problems. Embodiments of the present invention comprise compositions for organic, all-natural biocides with applications to control disease in plants, animals and humans.

BRIEF SUMMARY OF THE INVENTION

Embodiments of the present invention comprise organic natural compositions comprising: between approximately 0.0001% and approximately 20% oregano oil, water, and a natural, natural emulsifier to emulsify the oregano oil in the water and form a pesticide that when applied in an effective treatment dose kills plant pests. In one embodiment, the natural emulsifier is albumin at a ratio of between approximately 20 and approximately 5 parts oregano oil to 1 part albumin. In one embodiment a composition comprises between approximately 0.0005% and approximately 10% of oregano oil. In one embodiment, between approximately 0.001% and approximately 5% of oregano oil. In one embodiment the albumin is provided at a ratio of between approximately 15 and approximately 7 parts oregano oil to one part albumin. In one embodiment, the albumin is provided at a ratio of between approximately 12 and approximately 9 parts oil to 1 part albumin.

In a different embodiment, the natural emulsifier comprises natural saponins extracted from a desert plant, for example, of the genera *Yucca*, and between approximately 0.0005% and approximately 10% of oregano oil. In another embodiment, between approximately 0.001% and approximately 5% of oregano oil.

Another embodiment of the invention comprises an organic natural semisolid composition comprising between approximately 0.0001% and approximately 20% oregano oil, and a semisolid natural carrying medium to form a pesticide that when applied in an effective treatment dose kills plant pests. In one embodiment, the natural carrying medium is grain based flour selected from the group consisting of wheat, oat, rice, millet, and tapioca flour. In another embodiment, the composition further comprises an additive to prevent crumbling, for example, at a concentration ranging between approximately 0.001% and approximately 50%. In another embodiment, the additive is at a concentration of between approximately 0.01 and approximately 30%, or at a concentration of between approximately 0.1% and approximately 20%. In one embodiment, the additive is xanthum gum. In a different embodiment, the additive is guar gum. In one embodiment the composition comprises between approximately 0.01 and approximately 30% oregano oil. In another embodiment the composition comprises between approximately 0.1% and approximately 20% oregano oil.

In a different embodiment of the invention the composition's natural emulsifier is Tween 20.

A different embodiment of the invention comprises an organic and natural semisolid composition comprising between approximately 0.0001% and approximately 20% oregano oil, and a semisolid natural carrying medium to form a biocide that when applied to a mammal in an effective treatment dose kills mammal parasites. In one embodiment, the natural carrying medium is a gel such as Aloe Vera gel, or petroleum jelly.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention.

The drawings are only for the purpose of illustrating one or more preferred embodiments of the invention and are not to be construed as limiting the invention. Note, in the Tables 1 and 2 and in FIGS. 1-5, biocide formulations were based on oil from *Lippia berlandiere* (Mexican Oregano), and in FIGS. 6A and 6B formulations were based on oil from *Oreganum vulgare* (European Oregano).

FIG. 6A shows the live, motile nematode growing in absence of oil; and in 5B, two non-motile dead nematode in the presence of 1% oil;

DETAILED DESCRIPTION OF THE INVENTION

Figure 1:
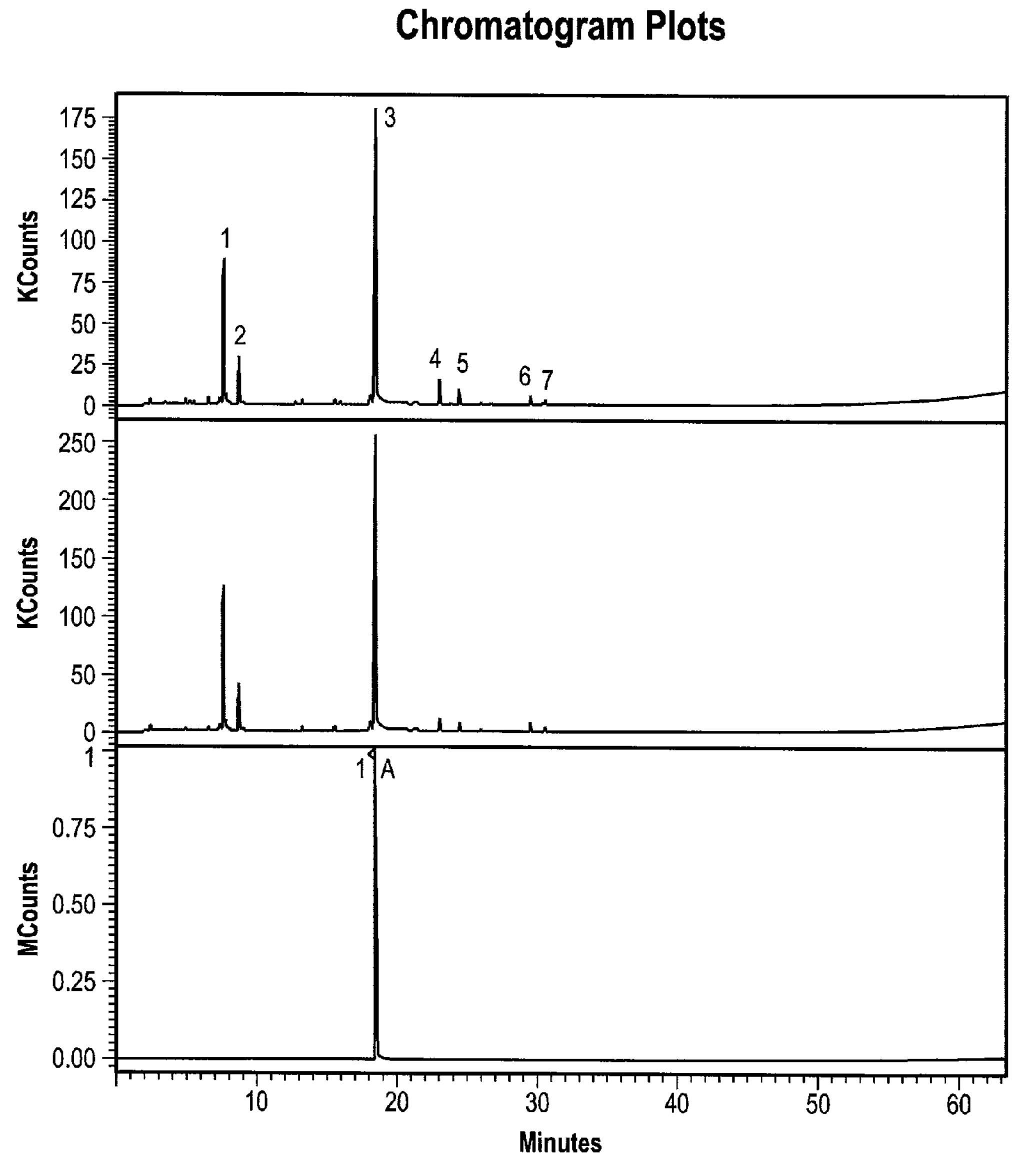
FIG. 1 shows the gas chromatography and mass spectrometry analyses of the biocide (top 2 spectra) as compared to a commercial standard of carvacrol (bottom spectrum)

In the following detailed description, numerous specific details are set forth in order to provide a thorough understanding of the embodiments of the invention. However, it will be understood by one of ordinary skill in the art that the embodiments may be practiced without these specific details. For instance, well known operation or techniques may not be shown in detail. Technical and scientific terms used in this description have the same meaning as commonly understood to one or ordinary skill in the art to which this subject matter belongs.

As used throughout the specification and claims, the term "surfactant" refers to compounds that lower the surface tension of a liquid, the interfacial tension between two liquids, or that act as detergents, wetting agents, emulsifiers, foaming agents, or dispersants. Similarly, solid and gel materials are used to dilute and solidify the essential oil in biocide formulations to control pathogens of plant, animal and human.

As used throughout the specification and claims, the term "emulsion" means a mixture of two or more liquids that are normally immiscible, for example oil and water.

As used throughout the specification and claims, the term "effective concentration" means the concentration of essential oils in aqueous, solid and gel materials used as biocide delivery media.

As used throughout the specification and claims, the term "effective treatment dose" means the quantity of biocide that effectively kills fungi, bacteria, viruses, nematodes, insects, etc., for treatment of infections in plants and animals.

Embodiments and compositions of the present invention comprise organic, natural biocide compositions comprising essential plant oils and combinations thereof delivered as a solid, gel, or liquid. Liquid formulations preferably comprise natural surfactants to emulsify the constituents and increase their effectiveness.

With regard to liquid formulations, the challenge to developing a natural biocide comprising essential oils in water is that generally, when water and oil are mixed together, for example by shaking the mixture, a dispersion of oil droplets is formed in the water. However, when the shaking stops, the phases start to separate. A third substance has to be added to the mixture to maintain the oil droplets dispersed in the water, i.e., a surfactant to act as an emulsifier is added to create a stable emulsion. The emulsifier positions itself at the oil/water interface and, by reducing the surface tension, has a stabilizing effect on the emulsion. A stable emulsion can be applied to crops, for example, by being sprayed more efficiently, and can remain active for a longer period of time since the phases do not readily separate. Alternatively, oil can be applied as solid when mixed with appropriate solidifying agents, or as a topical ointment when formulated using polymeric gels.

Embodiments for formulations disclosed herein use either Mexican or European oregano oil, which have similar effectiveness. In one embodiment of the invention, a composition comprises water and between approximately 0.0001% and approximately 20% of Mexican or European oregano oil, more preferably between approximately 0.0005% and approximately 10% of oregano oil, and most preferably between approximately 0.001% and approximately 5% of oregano oil. Different oil concentration ranges are preferably used for different applications for effective treatment doses, for example, 0.001% to 0.5% for bacterial and weak fungal pathogens; 0.1%-25% for more robust fungal pathogens; 0.1-10% for control of nematodes and insects, etc.

The oil is preferably emulsified in the water through a natural surfactant for a composition that when applied in an effective concentration kills plant pests, including but not limited to, fungi, bacteria, viruses, nematodes, insects, etc. In one embodiment called NMX-1, the natural emulsifier is albumin, at a ratio of between approximately 20 and approximately 5 parts oil to 1 part albumin; more preferably between approximately 15 and approximately 7 parts oil to one part albumin; and most preferably at a ratio of between approximately 12 and approximately 9 parts oil to 1 part albumin. Albumin can alternatively be used as a liquid or as a dry solid.

In another embodiment called NMX-2, a detergent, for example, Tween 20 or Sodium Dodecyl sulfate (SDS), is preferably added to the composition to improve emulsification and stability of the oil. In one embodiment, a composition preferably comprises water, oil, and between approximately 0.0001% and approximately 2% detergent, more preferably between approximately 0.0005% and approximately 1% detergent, and most preferably between approximately 0.001% and approximately 0.1% detergent.

Another embodiment, called NMX-3, of the present invention preferably comprises natural saponins from desert plants, for example, of the genera *Yucca* as emulsifying agents for the biocidal oil, used in the same proportions as described for albumin in the NMX-1 embodiment above.

In one embodiment, a composition is stored, sold, and distributed more conveniently in a concentrated form that can be diluted with water prior to application on site to be used as a biocide. The final concentrations and ratios of the concentrated product formulations are the same as described above.

In another embodiment, called NMX-4, a solid pellet form is preferably made from a solid, or semisolid carrying medium, such as, but not limited to, grain flours, e.g., wheat, oat, rice, millet, tapioca, and the like. Oregano oil is preferably diluted and "cut" into flours and diluted into final oil concentrations ranging from between approximately 0.001% and approximately 50%, more preferably between approximately 0.01 and approximately 30%, and most preferably between approximately 0.1% and approximately 20%. Preferably, the solid material carrying medium allows the slow release of the oil into the surrounding environment.

Figure 8A:
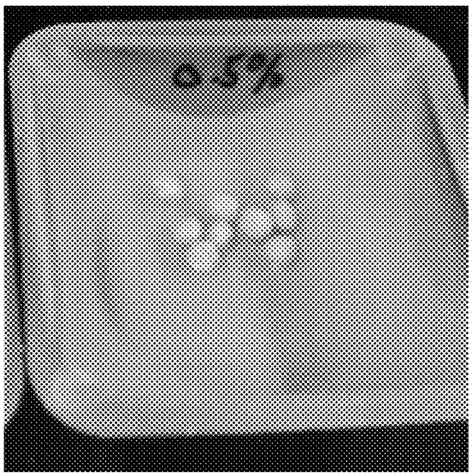
FIG. 8A is a photograph of a semisolid, slow-release formulation embodiment.

In order to make the solid embodiment formulations resistant to crumbling, additives or stabilizers, such as but not limited to, xanthum gum, guar gum, and the like, are preferably incorporated in concentrations ranging from between approximately 0.001% and approximately 50%, more preferably between approximately 0.01 and approximately 30%, and most preferably between approximately 0.1% and approximately 20%. The proportions of xanthum gum are preferably also varied in order to provide variable-release pesticide formulations, with 0.1%-1% xanthum gum giving fast-moderate release of the pesticide in the field, and 1-10% xanthum gum giving moderate to slow-release formulations. Optionally, the mixture comprises some water. FIG. 8A shows an example solid-based, slow-release formulation.

Figure 8B:
FIG. 8B is a photograph of a gel formulation embodiment.

In another embodiment, a composition is formulated for a salve for treatment of animals and/or humans, comprising oregano oil diluted into a gel, such as but not limited to, aloe vera gel, petroleum jelly, and the like. Preferably, concentrations of oil in the gel vary from between approximately 0.001% and approximately 50%, more preferably between approximately 0.01 and approximately 35%, and most preferably between approximately 0.1% and approximately 25%, depending on the various applications. FIG. 8B shows an example aloe vera-based formulation.

In another embodiment, a composition is formulated to apply to animal or human skin by diluting the oil in other oils such as soybean, safflower and olive oils and the like. Preferably, concentrations of the oregano oil in the other vegetable oils vary from between approximately 0.001% and approximately 50%, more preferably between approximately 0.01 and approximately 35%, and most preferably between approximately 0.1% and approximately 25%, depending on the various applications.

INDUSTRIAL APPLICABILITY

The invention is further illustrated by the following non-limiting examples.

Example 1

Referring to FIG. 1, the bioactive agents in Mexican oregano oil were identified by Gas Chromatography/Mass Spectrometry ("GC/MS"). The first two plots represent the two analyses of separate oil preparations and the last plot represents the spectrum of a pure carvacrol standard (Sigma). The most prevalent components in the Mexican oregano oil were identified by GC/MS library analysis to be: 1=cyclohexene-methyl cymene; 2=thymol; 3=carvacrol.

Example 2

Figure 2:
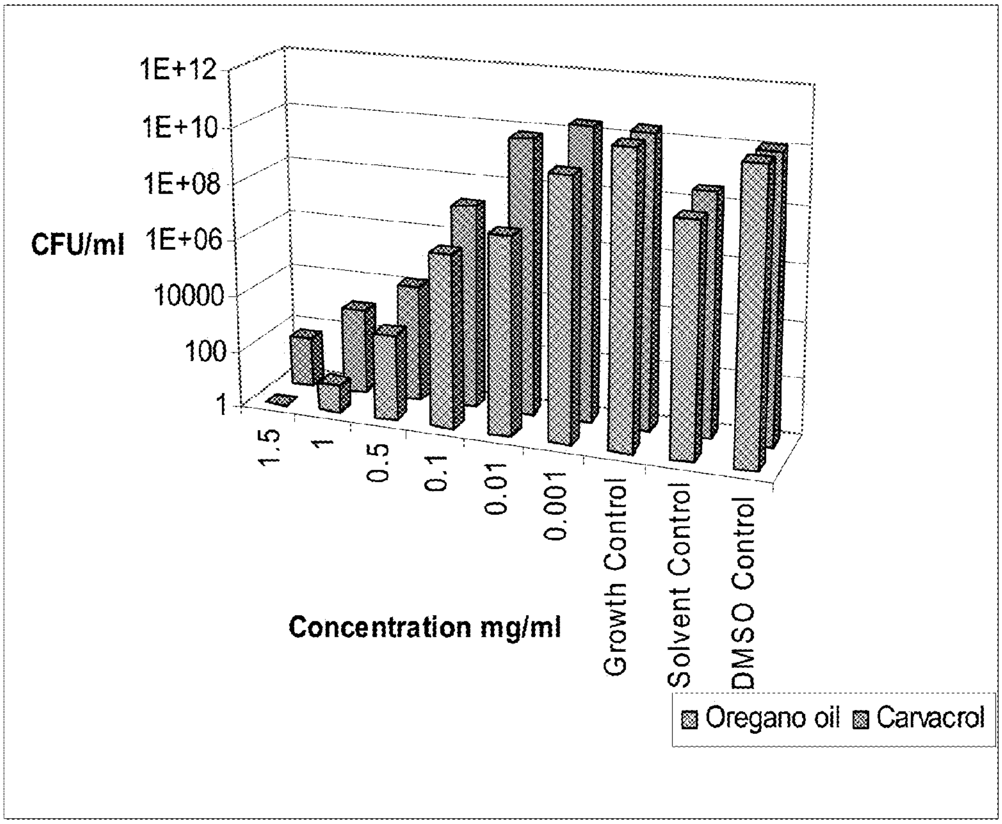
FIG. 2 shows the results of studies demonstrating the antimicrobial effect against the plant pathogen *Xanthomonas campestris* (the causative agent of Bacterial Spot Disease) using an embodiment of a biocide formulation compared to carvacrol.

When the most well-known biocide component of oregano oil, Carvacrol, was used in compositions of biocides, it was not as effective as the essential oil (see FIG. 2), indicating that there is synergistic effect when these agents work together in combination in the essential oil. In FIG. 2, the growth of *X. campestris* Provencia strain was assessed under different concentrations of Mexican oregano oil or pure carvacrol (dissolved in methanol solvent). The bars in the graph indicate the bacterial number (CFU) that was reached after 18 hours of incubation. At the same concentration of 0.01 mg/ml, oregano oil was significantly more inhibitory than carvacrol (p-value=0.009) indicating that, at equal concentrations, the biocide is more potent than carvacrol. Thus, a composition of biocide comprising oregano oil exerts synergistic effects, due, in part, to the multiple antimicrobial biochemicals that make up the oil (see FIG. 1).

Figure 3A:
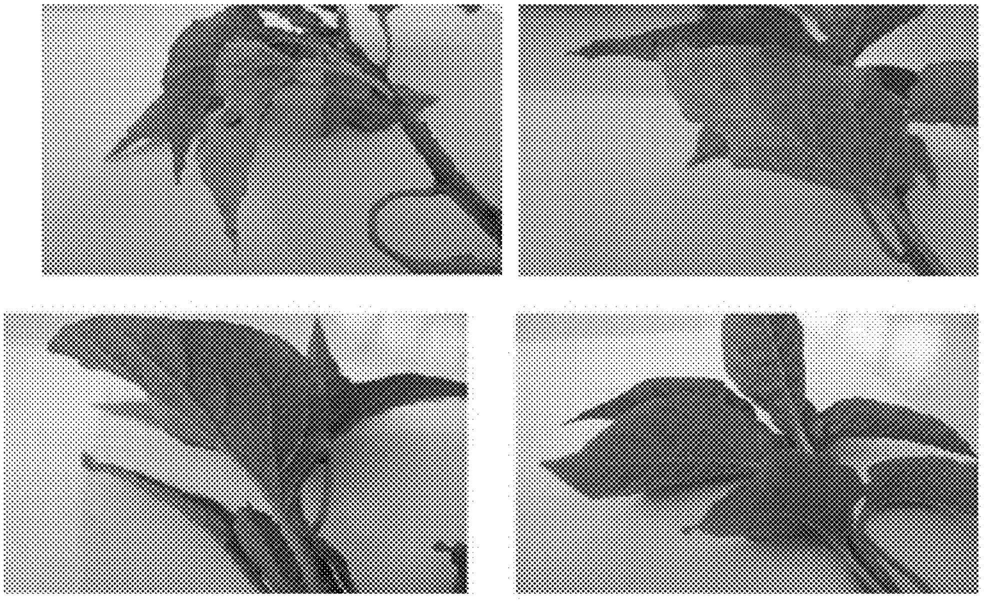
FIG. 3A. shows Jalapeno plants with and without symptoms of Bacterial Spot Disease caused by *X. campestris;*

The seeds of the greenhouse Jalapeno plants were infected with *X. campestris*, and, without the NMX spray, developed symptoms of bacterial spot disease. At 20 days and 50 days post germination, Jalapeno plants were sprayed with 0.1% NMX-1 oil using a squirt bottle adjusted to give a fine mist spray. The treatment of Jalapeno plants with low concentrations of oregano oil (0.1%) protected plants from Bacterial Spot Disease. In FIG. 3A, the photographs show Jalapeno plants infected with *X. campestris*, and plants without symptoms.

Figure 3B:
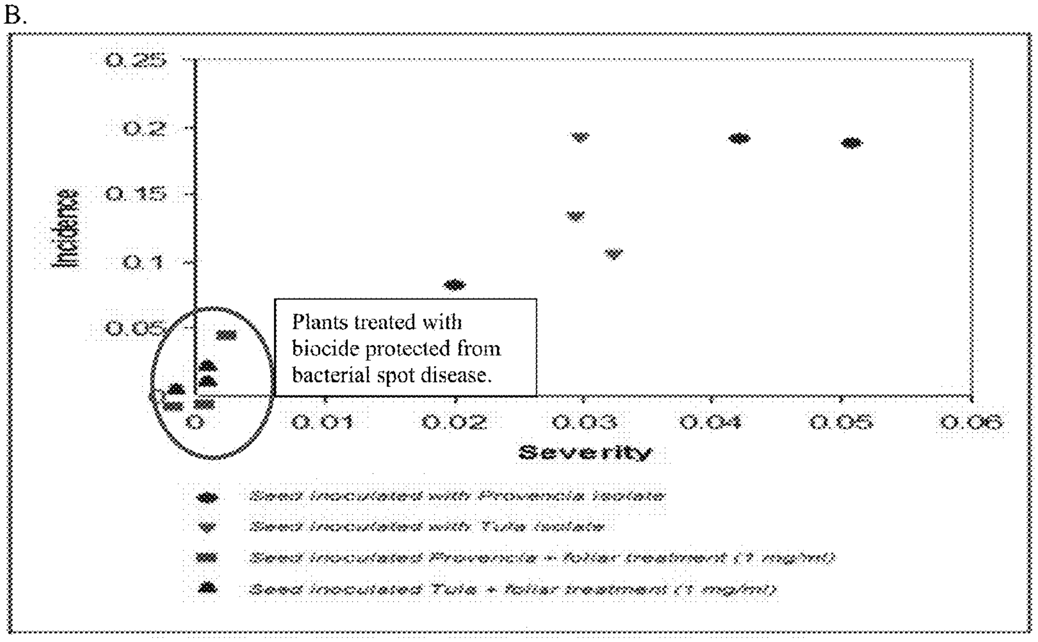
FIG. 3B shows the incidence and severity of Bacterial Spot Disease on Japapeno. Note the almost complete alleviation of symptoms when plants were treated with 0.1% of an embodiment of the present invention.

Referring to FIG. 3B, Jalapeno bacterial spot symptoms were quantified as to incidence and severity. Plants that were not foliar treated exhibited symptoms as shown in A, and plants that were foliar treated with a formulation of biocide comprising oregano oil 1 mg/mL (0.1%) showed little or no symptoms.

Example 3

Figures 4A, 4B, 4C, 4D:
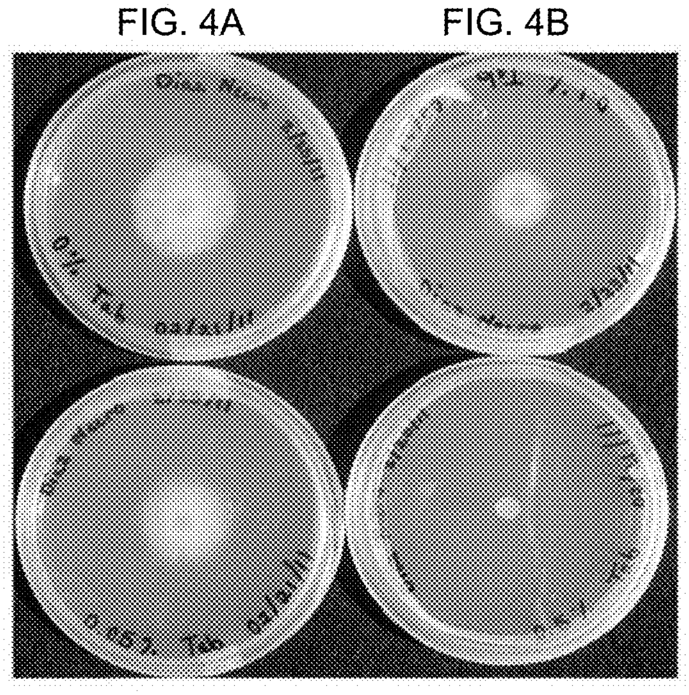
FIGS. 4A-D show photographs of agar plates inoculated with the plant pathogen *Phytothphera capsici* and comprising Mexican oregano oil at different concentrations (A=zero, B=0.1%, C=0.05% and D=0.5%)
Figures 5A, 5B, 5C, 5D:
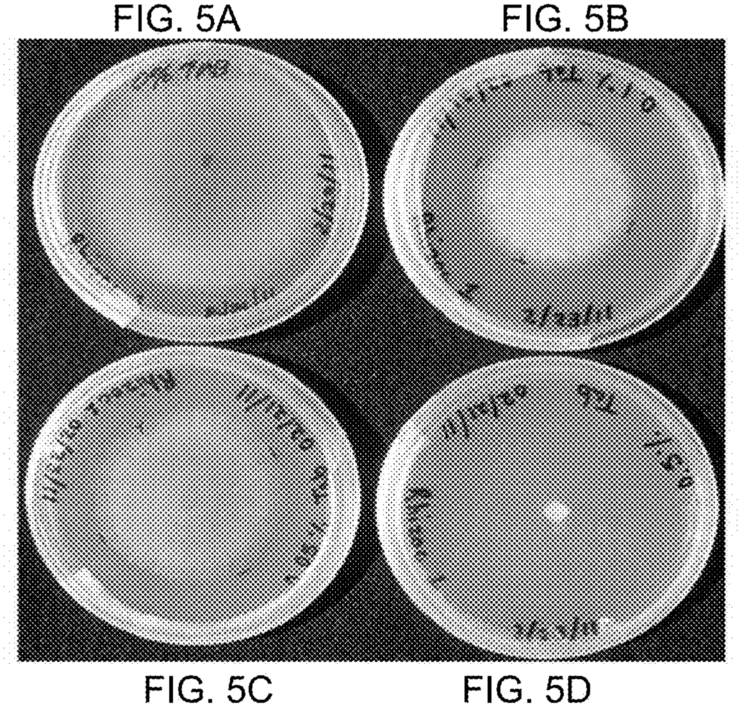
FIGS. 5A-D show agar plates inoculated with the plant pathogen *Rhizoctonia solani* treated with Mexican oregano oil at different concentrations (A=0, B=0.1%, C=0.05%, D=0.5%)

Referring to FIGS. 4-5, exposure to 0%, 0.05%, 0.1%, and 0.5% concentrations of Mexican oregano oil on agar plates demonstrated that the mycelial growth of *P. capsici* (FIG. 3D) and *R. solani* (FIG. 4D) are completely inhibited by oregano oil at a concentration of 0.50%.

Example 4

Figure 6A:
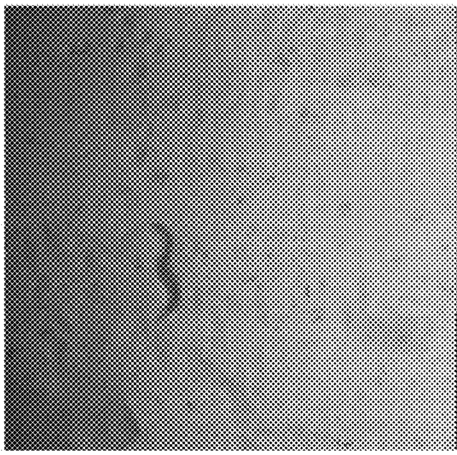
FIGS. 6A-B show the effect of 1% European oregano oil on growth and survival of the nematode, *Caenorhabditis elegans* after 3 days exposure.
Figure 6B:
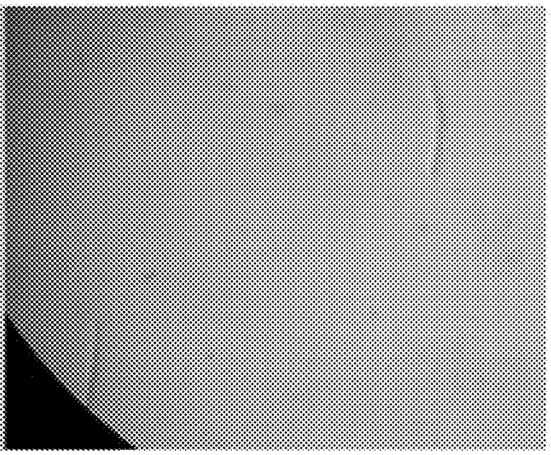

The essential oil was also found to be effective in controlling nematodes. Referring to FIG. 6, after a 3-day incubation, three of four nematodes survived in the absence of oregano oil, but no nematodes survived (see FIG. 6B) in the presence of a formulation of biocide comprising oregano oil at 0.1% or 1%. After 6 days, there still were no live nematodes in the presence of both concentrations of the oregano oil, but in its absence the nematode populations grew to 75-200 nematatodes.

Example 5

Figure 7:
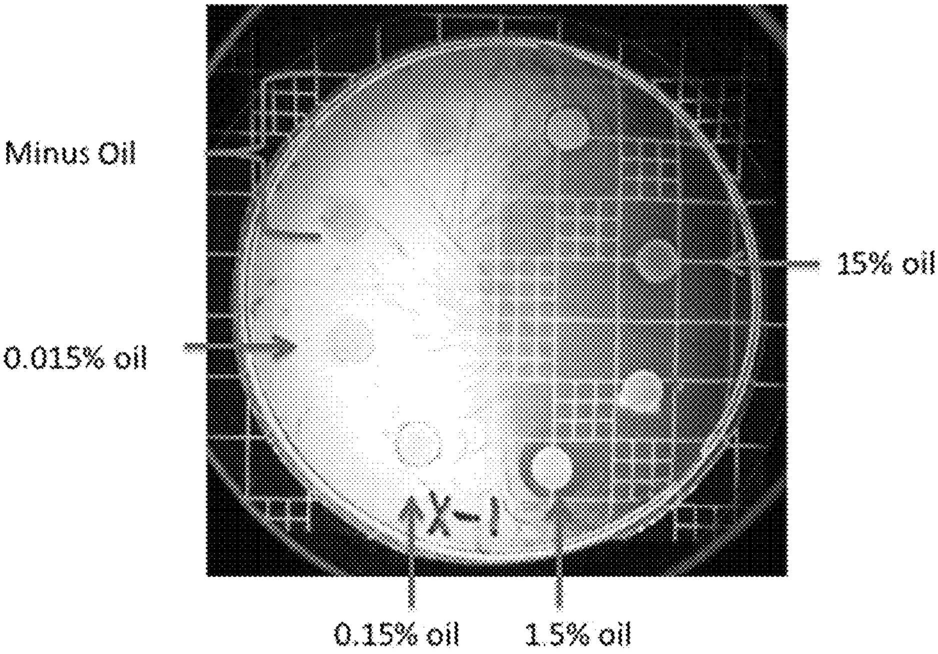
FIG. 7 is an agar plate inoculated with a bacterium isolated from a cow with symptoms of mastitis and exposed to varying concentrations of the oil.

An embodiment of the biocide was found to inhibit bacteria causing cow mastitis. In FIG. 7, an agar plate was inoculated with a bacterium isolated from the milk of a mastitis-infected cow in the presence of discs saturated with varying concentrations of oil. The bacterium grew in the absence of the oil (as demonstrated by the opaque colonial growth on the left), but was inhibited by varying concentrations of the oil.

Example 6

An embodiment of the biocide was found to have broad antimicrobial activities against plant, animal and human pathogens. Table 1 below shows the broad-spectrum antimicrobial effect of an embodiment for a natural biocide, inhibiting (bacteriostatic) or killing (bacteriocidal) bacteria (18 species) and fungi (2 species), including numerous human pathogens. The controls were grown using the same concentration of methanol (0.1%) which was used in the biocide. 20 of 20 test bacteria and fungi were either killed or significantly inhibited by the biocide, including representative plant, animal and human pathogens. The average optical density (O.D. 625 nm) of five replicate growth cultures was calculated, and are expressed as percent of growth relative to a minus-oil control. S=Strong inhibition≤50%, M=Moderate inhibition≤65%, W=Weak inhibition≤75% of control, NE=No effect>75% of growth relative to control. Note: 0.1 mg/mL=0.01% wt. to vol.

| Microorganism | Concentration of Oil (mg/ml) | Percent of Growth relative to Control (sd) | Inhibitory Score |
|---|---|---|---|
| *Bacillus cereus* | 0.1 | 12.8 ± 0.52 | S |
| | 0.01 | 49.20 ± 3.04 | S |
| | 0.001 | 78.88 ± 0.86 | NE |
| *Bacillus megaterium* | 0.1 | 23.38 ± 0.23 | S |
| | 0.01 | 84.82 ± 6.48 | NE |
| | 0.001 | 98.35 ± 0.74 | NE |
| *Bacillus subtilis* | 0.1 | 16.24 ± 0.01 | S |
| | 0.01 | 33.68 ± 0.05 | S |
| | 0.001 | 73.65 ± 0.01 | W |
| *Candida krusei* | 0.1 | 22.9 ± 1.36 | S |
| | 0.01 | 53.05 ± 2.17 | M |
| | 0.001 | 75.98 ± 1.38 | NE |
| *Corynebacterium pseudodiphteriae* | 0.1 | 12.47 ± 0.01 | S |
| | 0.01 | 34.70 ± 0.03 | S |
| | 0.001 | 64.77 ± 0.07 | M |
| *Geotrichum candidum* | 0.1 | 11.41 ± 0.64 | S |
| | 0.01 | 29.89 ± 1.46 | S |
| | 0.001 | 74.80 ± 3.70 | W |
| *Micrococcus luteus* | 0.1 | 11.16 ± 0.01 | S |
| | 0.01 | 18.91 ± 0.01 | S |
| | 0.001 | 42.72 ± 0.03 | S |
| *Streptococcus lactis* | 0.1 | 9.16 ± 0.02 | S |
| | 0.01 | 18.67 ± 0.01 | S |
| | 0.001 | 40.82 ± 0.01 | S |
| *Streptococcus pyogenes* | 0.1 | 26.64 ± 0.44 | S |
| | 0.01 | 45.23 ± 2.10 | S |
| | 0.001 | 113.37 ± 5.83 | + |
| *Staphylococcus aureus* | 0.1 | 11.43 ± 0.63 | S |
| | 0.01 | 44.97 ± 1.92 | S |
| | 0.001 | 76.05 ± 1.48 | W |
| *Alcaligenes faecalis* | 0.1 | 5.27 ± 0.01 | S |
| | 0.01 | 25.33 ± 0.05 | S |
| | 0.001 | 50.63 ± 0.02 | M |
| *Enterobacter cloacae* | 0.1 | 10.21 ± 0.62 | S |
| | 0.01 | 42.17 ± 2.39 | S |
| | 0.001 | 101.21 ± 8.83 | + |
| *Escherichia coli* | 0.1 | 23.64 ± 4.23 | S |
| | 0.01 | 40.52 ± 6.17 | S |
| | 0.001 | 98.77 ± 0.77 | NE |
| *Klebsiella pneumoniae* | 0.1 | 38.03 ± 0.07 | S |
| | 0.01 | 49.48 ± 0.03 | S |
| | 0.001 | 78.74 ± 0.01 | NE |
| *Neisseria perflava* | 0.1 | 10.67 ± 0.03 | S |
| | 0.01 | 38.61 ± 0.02 | S |
| | 0.001 | 84.60 ± 0.14 | NE |
| *Pseudomonas* | 0.1 | 21.96 ± 0.01 | S |

-continued

| Microorganism | Concentration of Oil (mg/ml) | Percent of Growth relative to Control (sd) | Inhibitory Score |
|---|---|---|---|
| *aeuruginosa* | 0.01 | 70.01 ± 0.06 | W |
| | 0.001 | 106.33 ± 0.33 | + |
| *Pseudomonas fluorescens* | 0.1 | 25.07 ± 0.56 | S |
| | 0.01 | 69.64 ± 1.96 | W |
| | 0.001 | 98.05 ± 1.15 | NE |
| *Proteus vulgaris* | 0.1 | 24.87 ± 0.03 | S |
| | 0.01 | 55.19 ± 0.02 | M |
| | 0.001 | 76.83 ± 0.01 | NE |
| *Serratia marcescens* | 0.1 | 10.89 ± 0.43 | S |
| | 0.01 | 92.19 ± 1.07 | + |
| | 0.001 | 97.54 ± 1.51 | + |
| *Shigella flexneri* | 0.1 | 22.01 ± 0.63 | S |
| | 0.01 | 79.84 ± 1.42 | NE |
| | 0.001 | 96.84 ± 2.82 | NE |

Table 2 below shows the bacteriocidal and bacteriostatic effects of formulations of biocide against four strains of a common plant pathogen, *Xanthomonas campestris*. The dose at which 50% of the *X. campestris* bacteria were killed by the bioagent (i.e., the $LD_{50}$) ranged between 0.1-0.5%. The causative agent of Bacterial Spot Disease, 4 of 4 strains of the *X. campestris* was killed or significantly inhibited by the biocide. The average O.D. 625 nm of five replicates was calculated and expressed as percent of growth relative to a minus-oil control. S=Strong inhibition≤50%, M=Moderate inhibition≤65%, W=Weak inhibition≤75% of control, NE=No effect>75% on growth relative to control. Note: 10 mg/mL=1% wt. to vol.

| *Xanthomonas campestris* strain | Concentration of Oil (mg/ml) | Percent of growth relative to control +/− Std Dev | Inhibitory score |
|---|---|---|---|
| Alvarez | 10 | 0 ± 0.43 | S |
| | 2 | 0 ± 0.36 | S |
| | 1 | 6.56 ± 2.2 | S |
| | 0.5 | 27.26 ± 5.9 | S |
| | 0.1 | 59.54 ± 1.4 | M |
| | 0.01 | 74.48 ± 0.62 | W |
| | 0.001 | 88.55 ± 0.5 | NE |
| Provencia | 10 | 0 ± 0.09 | S |
| | 2 | 0.21 ± 0.05 | S |
| | 1 | 5.01 ± 0.28 | S |
| | 0.5 | 6.25 ± 2 | S |
| | 0.1 | 59.57 ± 10.94 | M |
| | 0.01 | 72.13 ± 3.88 | W |
| | 0.001 | 91.63 ± 7.09 | NE |
| Deming | 10 | 0 ± 0.2 | S |
| | 2 | 0 ± 0.02 | S |
| | 1 | 5.96 ± 0.8 | S |
| | 0.5 | 35.10 ± 2.4 | S |
| | 0.1 | 66.06 ± 2.8 | W |
| | 0.01 | 102.62 ± 2.6 | NE |
| | 0.001 | 112.82 ± 0.8 | NE |
| Tula | 10 | 0 ± 0.07 | S |
| | 2 | 0 ± 0.06 | S |
| | 1 | 3.26 ± 0.24 | S |
| | 0.5 | 8.23 ± 0.33 | S |
| | 0.1 | 42.03 ± 4.9 | S |
| | 0.01 | 79.70 ± 3.9 | NE |
| | 0.001 | 96.11 ± 2.03 | NE |

The preceding examples can be repeated with similar success by substituting the generically or specifically described reactants and/or parameters of this invention for those used in the preceding examples. Note that in the specification and claims, "about" or "approximately" means within twenty percent (20%) of the numerical amount cited.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A sprayable, slow release emulsion pesticide comprising:

between approximately 0.0001% wt. to vol. and approximately 20% wt. to vol. Mexican oregano (*Lippia berlandiere*) essential oil;

water; and a natural emulsifier, the natural emulsifier being saponins extracted from a plant of the genus *Yucca*, in a ratio of between approximately 5 parts vol. % and approximately 20 parts vol. % of said oregano oil to one part of said natural emulsifier to emulsify said oregano oil in said water and form said sprayable, slow release emulsion pesticide that when sprayed onto a plant in an effective treatment dose kills spinach downy mildew pathogens without injuring the plant.

2. The sprayable, slow release emulsion pesticide of claim 1 comprising between approximately 0.0005% wt. to vol. and approximately 10% wt. to vol. of oregano oil.

3. The sprayable, slow release emulsion pesticide of claim 1 comprising between approximately 0.001% wt. to vol. and approximately 5% wt. to vol. of oregano oil.

4. The sprayable, slow release emulsion pesticide of claim 1 wherein said emulsifier is in a ratio of between approximately 7 parts vol. % and approximately 15 parts vol. % of said oregano oil to one part of said natural emulsifier.

5. The sprayable, slow release emulsion pesticide of claim 1 wherein said emulsifier is in a ratio of between approximately 9 parts vol. % and approximately 12 parts vol. % of said oregano oil to one part of said natural emulsifier.

6. The sprayable, slow release emulsion pesticide of claim 1 wherein 10 parts of said oregano oil are combined with 1 part of said natural emulsifier and are diluted in said water for said emulsion pesticide to comprise a final concentration of between about 0.01% by vol. and about 5% by vol. of said oregano oil.

7. The sprayable, slow release emulsion pesticide of claim 6 wherein said emulsion pesticide when sprayed onto a jalapeno plant in an effective treatment dose kills bacterial spot disease without injuring said jalapeno plant.

* * * * *